United States Patent [19]

Kása et al.

[11] Patent Number: 4,625,732
[45] Date of Patent: Dec. 2, 1986

[54] APPARATUS FOR MEASURING THE ACTUAL PSYCHOPHYSIOLOGICAL CONDITION

[75] Inventors: Zoltán Kása; Mihály Ágoston, both of Budapest; László Bognár, Kecskemét; János Hideg, Budapest; Péter Remes, Kecskemét; László Hiros, Budapest, all of Hungary

[73] Assignee: Medicor Muvek, Budapest, Hungary

[21] Appl. No.: 553,382

[22] Filed: Nov. 18, 1983

[30] Foreign Application Priority Data

Jun. 15, 1983 [HU] Hungary ............... 2132/83

[51] Int. Cl.⁴ ........................... A61B 5/02; A61B 5/05
[52] U.S. Cl. .................................... 128/670; 128/687; 128/734; 128/905
[58] Field of Search ............... 128/665–667, 128/670, 687, 689, 734, 905

[56] References Cited

U.S. PATENT DOCUMENTS

| | | | |
|---|---|---|---|
| 3,575,162 | 4/1971 | Gaarder | 128/905 X |
| 3,727,604 | 4/1973 | Sidwell et al. | 128/905 X |
| 4,110,918 | 9/1978 | James et al. | 128/905 X |
| 4,125,111 | 11/1978 | Hudspeth et al. | 128/689 |
| 4,184,485 | 1/1980 | Agoston | 128/905 X |

Primary Examiner—Donald R. Valentine
Attorney, Agent, or Firm—Handal & Morofsky

[57] ABSTRACT

Apparatus is provided for measuring the actual psychophysiological condition of a subject. The apparatus may be hand held and includes finger engaging sensor means, a keyboard and a display means. Various block elements are included for measuring skin conductance, actual mental condition and actual physical condition. An arithmetical and logical unit is associated with the conditioning blocks for determining respective weighted sums of measured results provided by the blocks.

4 Claims, 10 Drawing Figures

APPARATUS FOR MEASURING THE ACTUAL PSYCHOPHYSIOLOGICAL CONDITION

The invention relates to the field of biophysical examinations, more particularly to a method and apparatus for measuring the actual psychophysiological condition of a subject. Under the term "psychophysiological condition" the complexity of the actual emotional, mental and physical conditions is understood.

It has been experienced for a long period of time that the fitness or productivity of the people has a fluctuating character and this fluctuation is often attributed to periodic changes experienced in the emotional, mental and physical spheres. There are hypotheses which try to teach that such fluctuations are periodical with different period times and phases, and tests are provided which indicate whether in a given moment a particular subject is in more or less fit condition. Although such theories lack scientific basis, the fluctuation of the psychophysiological condition should be accepted to be an experimental reality, and the indication of the degree of such a condition may be beneficious for many individuals.

There are several ways for the measurement of the actual emotional, mental or physical conditions, these ways are, however, valid under certain circumstances only, i.e. they are not true for the whole population and are not reproducable i.e. not sufficiently objective. In addition to such limitations these measurements require specialised instrumentation. The instruments used for such purposes are bulky, expensive and not easily transportable.

There is a definite need for a small-sized portable instrument which can indicate the degree of the actual psychophysiological condition of a subject which supplies objective and reproducable qualifications and does not require a high degree of skill from the user.

The measurement of the emotional condition is generally related to skin conductance measurements. Although there are several ways for measuring the skin conductance, they all have some disadvantages. The main problem lies in that direct current sensors are generally not usable, because the direct current flowing through a portion of the human body tends to cause polarization phenomena in the particular body area which can falsify the result. In order to overcome the polarization problems, alternating signals are used for skin conductance detection. The processing of AC voltages has its own drawbacks which lie mostly in the reduced sensitivity.

During physical condition measurements the heart rate of a subject is often measured. Such measurements are made generally by means of pulse sensors including a light emitting diode and a light sensitive transistor arranged to give place for a finger therebetween. When the hand of the subject is moved (which is generally the case during a physical condition test), the blood stream through the finger varies within wide limits, and under highly changing circumstances it is hard to obtain uniform definite pulse signals. It is often experienced that the pulse signal gets noisy or fades away when the subject is moving, which makes such tests difficult.

It is a first object of the present invention to provide an apparatus which can objectively determine all factors of the actual psychophysiological condition on the basis of objective measurements, which is sufficiently small to be held in hand and which can be handled easily.

Further objects of the present invention lie in that novel methods and apparatus should be made for the particular condition measurements which can be used together as factors of a complex psychophysiological measurements, or can be used in themselves for particular condition measurements such as the measurement of mental, emotional and physical conditions.

A further object of the invention lies in providing an improved apparatus for detecting skin conductance, which can highly facilitate the emotional condition measurements.

A still further object of the invention lies in providing a novel circuit arrangement for heart rate measurements which can provide a uniform detecting sensitivity even if the hand is moved, whereby the physical condition tests are facilitated.

According to a first aspect of the invention an apparatus is provided for measuring the actual psychophysiological condition of a subject which comprises:
a case to be held in hand;
sensors engaging fingers holding the case to detect skin conductances;
a pulse sensor engaging a finger holding the case;
a keyboard arranged in a surface of the case with identical keys;
a display arranged in the surface with display segments associated with respective ones of the keys;
a block for determining the actual emotional condition which comprises:
  a skin conductance measuring block connected to the sensors,
  a feedback unit for delivering an indication for the subject in response to actual skin conductance values
a block for determining the actual mental condition which comprises:
  a pulse source for providing light pulses on the display segments in a random distribution,
  an audio signal source providing audio signal together with selected ones of said light pulses according to a random selection,
  a means for detecting the simultaneous activation of a pair of associated key and display segment,
a block for determining the actual physical condition which comprises:
  a heart rate measuring means associated with the pulse sensor,
  a means for determining the efficiency of repeated physical excercises made by the subject, and
an arithmetical and logical unit associated with the conditions determining blocks for determing respective weighted sums of measuring results provided by the blocks.

While this apparatus is capable of measuring the three spheres of the psychophysiological condition, namely the emotional, mental and physical ones, the individual blocks associated with the respective spheres can be used also as independent instruments for measuring the particular condition.

According to a further aspect of the invention a method has been provided for determining the cathegory level of the actual emotional condition of the subject, which comprises the steps of inducing the subject to perform an autogen training based on a biofeedback in which he or she already has at least some experience in a first phase for a predetermined time counted from a starting moment, recording a representation of the feedback value in said starting moment, giving a task for the subject that in the first phase a relaxed condition should be reached, recording the actual value of the feedback representation in the ending moment of the first phase, carrying out the autogen training in a second phase immediately following the first phase for a second predetermined time, in which giving a task for the subject to reach an active condition, recording the feedback representation in the end moment of the second phase, and determining the cathegory level on the basis of a linear combination of the relative changes of the recorded feedback representations during the phases.

According to a further aspect of the invention a method has been provided to determine the actual mental condition of a subject, comprising the steps of providing a random sequence of a predetermined number of light signals for the subject, in which the light signals are allocated to a predetermined number of display segments in a random distribution with uniform probability of activating any of the segments, these segments have identical shapes and each of them is associated with respective keys, instructing the subject to push the key associated with the flashing one of the segments when the flashing is percepted, providing acoustical signals together with selected ones of the light signals according to a random selection, instructing the subject not to push any key when an acoustic signal is perceived, measuring the sum of reaction times defined between the moments of the establishments of the light signals and the moments of pushing the associated key, measuring the number of right pushing movements and the number of effective acoustic blockings, and the mental condition is cathegorized according to the relation of a weighted sum of the three measured values to predetermined threshold values.

In a further aspect of the invention a method has been provided for determining the cathegory level of the physical condition of a subject, comprising the steps of instructing the subject to perform a repetitive sequence of predetermined gymnastical excercises which impose a physical load, sensing the occurrence of each excercise, detecting the heart rate of the subject, recording the heart rate in the end moment of said sequence, instructing the subject following the end moment to relax for a predetermined time, recording the heart rate value in the end moment of the relaxation period, and providing the weighted sum of the efficiency of the accomplishment of the excercises, of the first recorded heart rate, and of the relative decrease of the heart rate during the relaxation period to define a value characteristic to the actual level of the physical condition.

According to an other aspect of the present invention a circuit arrangement has been provided for measuring the skin conductance, comprising a pair of sensors engaging a body surface, a resistor with known resistance, a switching means for applying a constant direct voltage alternatively on the sensor or on the resistor, a measuring means for determining the current flowing through the sensors and through the resistor under the effect of the voltage, and evaluating means connected to the measuring means, which on the basis of the known resistance value and of the measured current values provides the representation of the conductance defined between the sensors.

In accordance with a still further aspect of the invention a circuit arrangement has been provided for measuring the heart rate of a subject comprising: a pulse sensor, including a light emitting diode and a light sensitive transistor with current depending of an incident light flux from the light of the diode following passage through a finger of the subject; a means for determining the current flowing through the diode; a current generator coupled in series with the light sensitive transistor; a regulating means with an input controlled by the difference of the current flowing through the transistor and the current of the current generator, the regulating means has integrating properties with a time constant of about 1 to 2 s, the output of the regulating means is coupled to the current determining means to adjust the current thereof.

The invention will now be described in connection with exemplary embodiments and examples thereof, in which reference will be made to the accompanying drawings. In the drawing

Figure 1:
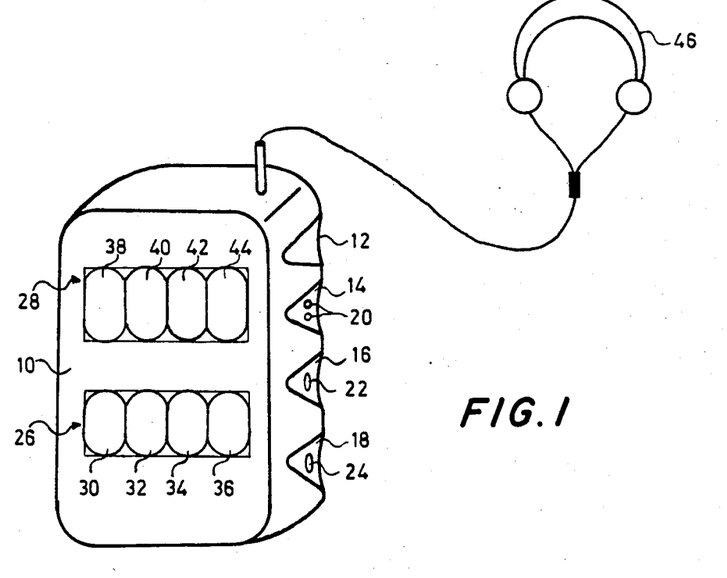
FIG. 1 shows the perspective view of the apparatus according to the invention for measuring the actual psychophysiological condition.

FIG. 1 shows a simplified perspective view of an embodiment of the apparatus according to the present invention. The apparatus comprises a small compact case 10, which, during operation can and should be held in hand. In one side wall of the case 10 recesses are made for accomodating the fingers, of which recesses 12, 14, 16 and 18 are shown in FIG. 1. A recess for the thumb is made in the other side of the case 10.

A pulse sensor 20 is arranged in one of the recesses 14 whereas sensors 22, 24 for skin conductance measurements are arranged in the two neighbouring recesses 16 and 18. A pair of zones 26 and 28 of equal design are provided one beneath the other on the front face of the case 10 and each of them is split up into four parts. Four identical keys 30, 32 and 36 are arranged in the lower zone 26 which can be actuated separately. The upper zone 28 comprises four identical display segments 38, 40, 42 and 44.

In the constructional design it is of importance that the relationship between the corresponding fields in the two closely arranged zones 26 and 28 can be established easily i.e. by a short glance which means e.g. that the functional relationship between the key 30 and the display segment 38 should be unmistakably evident for any user.

An appropriate socket is arranged in the upper wall of the case 10 for the connection of a head-phone 46.

For the sake of better visualisation the other handling means (like the on-off switch, etc.) are not shown in FIG. 1. It is preferable if the various handling organs are arranged elsewhere than the face plate in order that their presence can not disturb the functional relationship between the fields in the zones 26 and 28.

Figure 2:
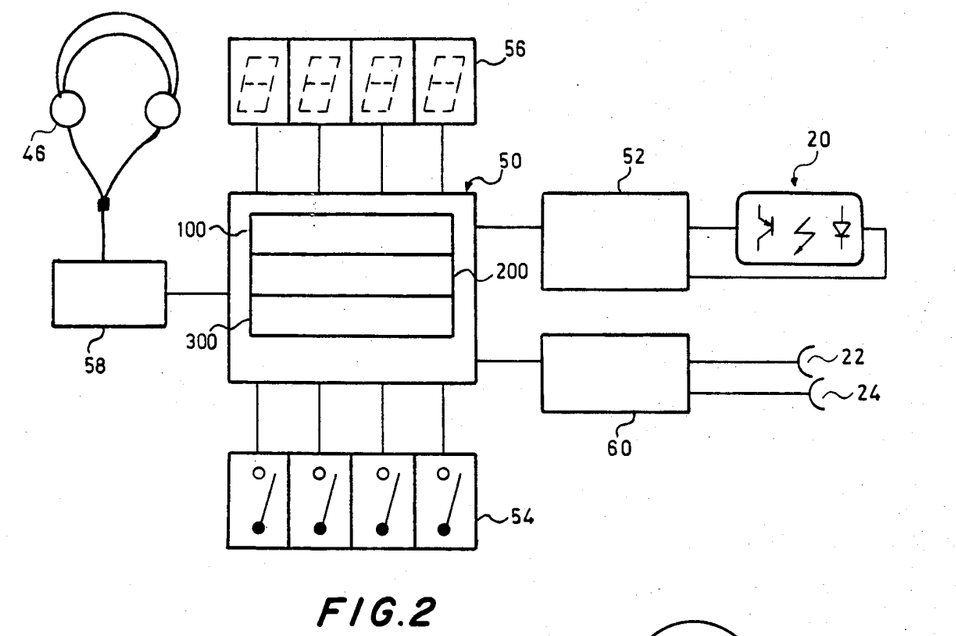
FIG. 2 shows the general block diagram of the apparatus shown in FIG. 1.

FIG. 2 shows the overall block diagram of the apparatus shown in FIG. 1. The main part of the apparatus is formed by a central control and calculating block 50 which can be divided in three main functional units i.e. emotional condition examining unit 100, mental condition examining unit 200 and physical condition examining unit 300. The central control and calculating block 50 can be implemented by a programmed microprocessor.

A pulse rate measuring block 52 and a skin conductance measuring block 60 are coupled to the central control and calculating block 50, and respective inputs of these blocks 52 and 60 are coupled to the pulse sensor 20 and to the sensors 22 and 24.

A display 56 comprising the display segments 38 to 44 in the zone 28 is also coupled to the central control nad calculating block 50. The head-phone 46 is connected through an acoustic coupler 58 to the central control and calculating block 50.

The operation of the apparatus according to the invention will be described in connection with the description of its respective functional units.

Now reference will be made to FIG. 3 which shows the functional block diagram of the emotional condition examining unit 100.

A biological feedback system has been provided for the subject to be examined, which enables practicing an autogen training by which the subject reaches a rest condition following an active starting state and a further active state from the rest condition. Such kind of autogen training can utilize the feedback of the relative activity of the alpha waves in the EEG spectrum, the feedback of the skin conductance or in given cases the feedback of the body temperature. From the point of view of the constructional design of the biofeedback system, of its handling facilities and of the efficiency, duration and feasibility for learning of the autogen training, it is believed that the feedback of the skin conductance can be considered to be the most preferable of all possible other kinds of feedback, therefore FIG. 3 shows the unit 100 as based on skin conductance feedback.

The subject under examination holds the apparatus shown in FIG. 1 in one of his or her hands, and his or her fingers touch the sensors 22, 24, and a skin conductance measuring block 60 measures the skin conductance. The output of the skin conductance measuring block 60 supplies the skin conductance level referred to hereinafter as SCL, and this output is coupled to input of a sample and hold circuit 102, to input of a divider 104 and to input of a multi-position controlled switch 106.

The output of the divider 104 is connected to the acoustic coupler 58 which latter is coupled to the head-phone 46. It is preferable, if the output of the divider 104 which delivers a digital value representing the frequency of the audio signal is coupled also to the display 54 for digitally displaying this value. The divider 104 has a second input coupled to the output of the sample and hold circuit 102 to receive the digital value of the sampled SCL signal.

The operation of the emotional condition examining unit 100 is controlled by control unit 108 having respective outputs coupled through line 110 to an input of the sample and hold circuit 102 which determines the sampling moment, through line 112 to control input of the controlled switch 106 and through line 114 to starting input of a first timer 116.

The controlled switch 106 has three outputs coupled to respective inputs of first, second and third sample and store circuits 118, 120 and 122, and the outputs of these circuits are coupled to inputs of an arithmetical and logical unit 124. A further input of the arithmetical and logical unit 124 is connected to a constant memory 126 which stores the constant values required for the calculations.

The output of the arithmetical and logical unit 124 is connected to a first input of a digital comparator 128 which has a second input coupled to a second constant memory 130 which stores treshold values required for the comparison. The output of the digital comparator 128 is coupled to display 56a which can be formed by any of the display segments 38 to 44.

The control unit 108 is connected also to a second timer 134 started by the output of the first timer 116. There is provided a start key 132 for starting the operation of the emotional condition examining unit 100 which can be formed by any of the keys 30 to 36.

The determination of the actual emotional condition is carried out as follows.

It is supposed that the subject under test has already some experience in using the apparatus according to the invention i.e. he or she can perform an autogen training based on the SCL feedback.

In the beginning of the test the apparatus will be taken in hand and the task lies in that after pushing the start key 132 he or she should try to get in a relaxed condition. In the starting moment the sample and hold circuit 102 receives a sampling command through the line 110 from the control unit 108, and stores the starting SCL value (moment $t_0$ in FIG. 8) supplied by the output of the skin conductance measuring block 60. In the two inputs of the divider 104 there is the same digital number and their quotient is therefore unity. In this way the input of the acoustic coupler 58 receives a digital number associated with a basic audio frequency which can be e.g. 300 Hz. Owing to the division and the normalization in the starting moments of each test, the same basic frequency can be heard in the head-phone 46 which is independent of the actual SCL value.

If during the autogen training the subject starts to get less active and more relaxed, then the SCL value decreases. The divider 104 delivers a digital number representing the quotient of the actual SCL value and the starting SCL 1 value, and this number will set the acoustic coupler 58 to generate a lower tone. A decrease in the SCL value e.g. by 10% compared to the starting value results in the decrease of the starting audio frequency of 300 Hz by 30 Hz.

During this phase of the autogen training the subject has the task of deepening the audio frequency with all effort. The digital value of the actual frequency can even be displayed on the display 56.

The starting SCL 1 value will be stored in the moment $t_0$ not only in the sample and hold circuit 102, but through the controlled switch 106 also in the first sample and store circuit 118. Also in the starting moment $t_0$ the first timer 116 will be started through the line 114 to provide a predetermined timing T1 e.g. between 1 and 5 minutes.

Figures 8, 9:
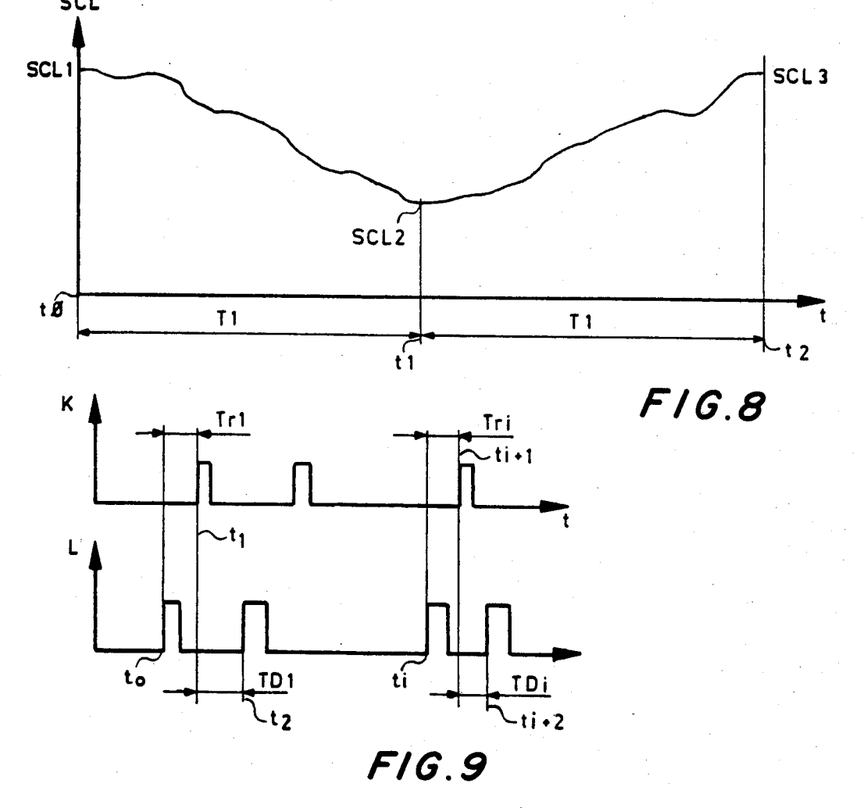
FIG. 8 shows the time curve of the skin conductance during the emotional condition test.
FIG. 9 shows light and key pulses versus time used for the mental condition test.

FIG. 8 shows the time diagram of the SCL value. At the ending moment $t_1$ of the timing T1 the first timer 116 delivers a signal for the control unit 108 and the relaxation phase is finished.

The control unit 108 sets the controlled switch 106 in a further position and in this moment t₁ the actual SCL 2 value will be read in the second sample and store circuit 120. Simultaneously the sample and hold circuit 102 receives through the line 110 a new sampling command and the SCL 2 value will be held therein. The two inputs of the divider 104 will be again identical, and the tone will take the starting frequency, i.e. 300 Hz. This change indicates for the subject the end of the relaxation phase. This indication can be underlined e.g. by flashing a digit on the display 56. In the moment t₁ the first timer 116 starts the timing of the second timer 134 which has preferably the same timing duration.

The subject under test knows that after the end of the relaxation phase the task will be changed and the active condition should be regained as soon as possible that is the autogen training should be practiced in reverse direction. The subject strives to increase and not to decrease the tone pitch, whereby the skin conductivity will also increase. At the end moment t₂ of the activation phase the second timer 134 delivers a signal, the control unit 108 sets the controlled switch 106 in a further position, and the third sample and store circuit 122 will store the actual SCL 3 value. Now the emotional condition examination test is finished and the subject is informed thereabout by means of the display 56.

The emotional condition depends on the extent of contribution of the subject in carrying out the relaxation and later the activation tasks. The emotional condition is favourable if this contribution was succesful, and it is not favourable if it was not.

On the basis of experimental tests it can be stated that the extent of the succesful contribution can also be expressed in numerical form, e.g. as follows:

$$S_1 = a_{11}SCL1 + a_{12}\frac{SCL1 - SCL2}{SCL1} = a_{13}\frac{SCL3 - SCL2}{SCL2} \quad (1)$$

The coefficients $a_{11}$, $a_{12}$ and $a_{13}$ in formula (1) depend on the sex, age, occupation of the subject under test and this values are stored in the constant memory 126.

All values required for the calculation defined in formula (1) are reported to the arithmetical and logical unit 124, which delivers therefore the value $S_1$ in its output.

The apparatus according to the invention is capable of delivering the value $S_1$ directly, in the practice, however, it is sufficient to know whether the actual emotional condition is high, medium or low. The constant memory 130 stores two treshold constants $K_{11}$ and $K_{12}$ with which the value $S_1$ will be compared in the digital comparator 128.

If the value $S_1$ is higher than the first constant $K_{11}$, then the emotional condition is favourable, i.e. high, if the value $S_1$ falls between the two constants $K_{11}$ and $K_{12}$, the emotional condition is on medium level, and the emotional condition is low, if $S_1$ is smaller than the constant $K_{12}$. The display 56a shows an indication corresponding to these three possible states.

For an average population the typical values of the above coefficients and constants are as follows:

$a_{11} = -0.4$ $a_{12} = -40$ $a_{13} = +20$ $K_{11} = +5.2$
$K_{12} = -1.6$

Figure 3:
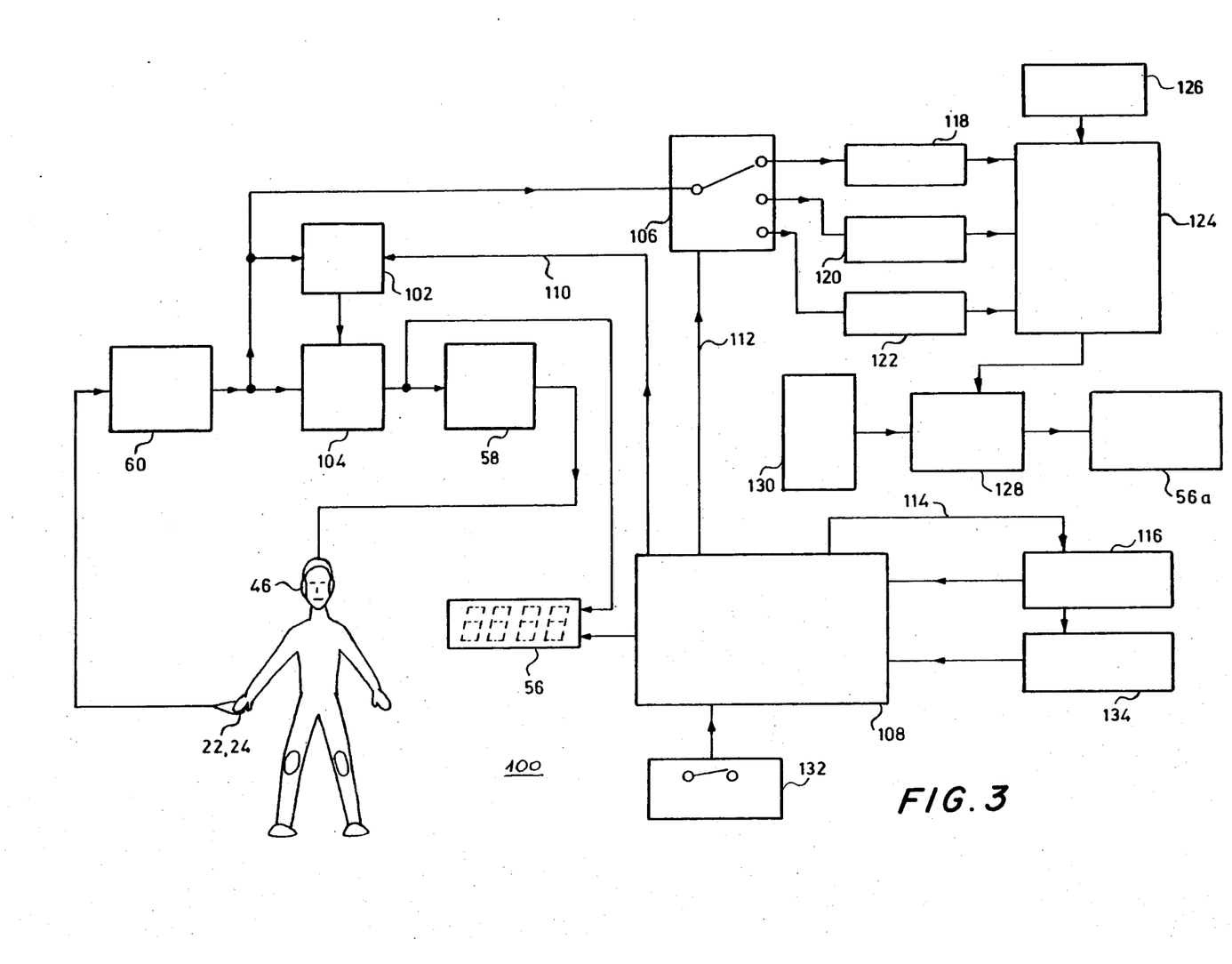
FIG. 3 shows the detailed block diagram of block 100 of FIG. 2.

The emotional condition can be examined not only by the unit 100 shown in FIG. 3 but by a number of alternative arrangements. From the aspect of the present invention it has an importance only that the level of the emotional condition is defined as the efficiency of an autogen training comprising a first phase directed to reach a relaxed state in a prescribed time and a second phase for reaching an active condition again.

Although, it is believed that the arrangement shown in FIG. 3 can be easily implemented for the man skilled in the art on the basis of the foregoing description, reference will be made now to FIG. 6, in which a preferable embodiment of the skin conductance measuring block 60 is shown, since this embodiment is believed to can measure the SCL value easier and with a higher accuracy than the conventionally used SCL meters.

Figure 6:
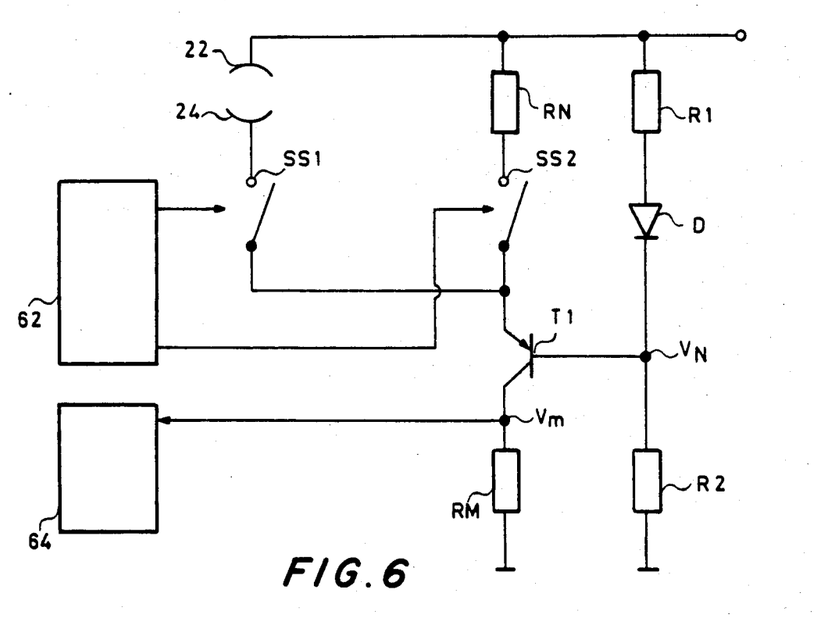
FIG. 6 shows a circuit arrangement usable for measuring the skin conductivity

In FIG. 6 a transistor T1 is shown with an emitter circuit comprising alternatively controlled switches SS1 and SS2, by which the SCL sensors 22, 24 or a resistor $R_N$ are coupled to the emitter. The transistor T1 has a base circuit comprising resistors R1, R2 and a diode D for compensating temperature dependency. The so constructed base attenuator provides a base voltage $V_N$ smaller than the supply voltage $V_{cc}$.

A voltage $V_m$ can be measured on collector resistor $R_M$ of the transistor T1, the value of which in the on-condition of the switch SS2 can be expressed as:

$$V_{m2} = R_M \frac{V_N}{R_N}. \quad (2)$$

If the resistance of the skin between the sensors 22 and 24 has a value of $R_x$, then in the on-state of the switch SS1 this voltage can be expressed as:

$$V_{m1} = R_M \frac{V_N}{R_x}. \quad (3)$$

When $R_M$ is expressed from the formulae (2) and (3) and the two expressions are made equal, the following equation is obtained:

$$V_{m2}R_N = V_{m1}R_x$$

$$\frac{1}{R_x} = SCL = \frac{V_{m1}}{-V_{m2}R_N}.$$

The switches SS1 and SS2 are alternatively controlled by a controller 62 in such a way that the switch SS1 is substantially shorter in on-condition that the other switch SS2. The voltages $V_{m1}$, $V_{m2}$ defined in formula (4) can be measured at the collector of the transistor T1 in the corresponding switch positions, and an analog to digital converter 64 converts these voltages in digital form, and the remaining parts of the skin conductance measuring block 60 use these digital values to provide the required SCL value.

The advantages of the circuit of FIG. 6 lie in that the voltage between the sensors 22, 24 is always the same during each measurement, therefore there is no need for the application of alternating voltages, because during the long on state of the switch SS2 the possible polarization phenomena are decayed, and from the direct current direct signal processing an increased sensitivity is reached compared to conventional circuits using alternative signal components only.

Apart from these advantages further benefits come from the simple and cheap construction of the circuit.

Now reference will be made to FIG. 4, which shows the functional block diagram of a preferable embodiment of the mental condition examining unit 200 (FIG. 2).

The mental condition will be established from the weighted value $S_2$ of the information processing ability of the subject under test. The value $S_2$ is obtained from one-in-four type reaction measurements carried out under predetermined conditions, in which an acoustic blocking stimulus is applied, and the rate of stimulus generation is gradually increased. Also in this examination it is supposed that the subject under test is familiar with the apparatus and has already some practice in its use.

Figure 4:
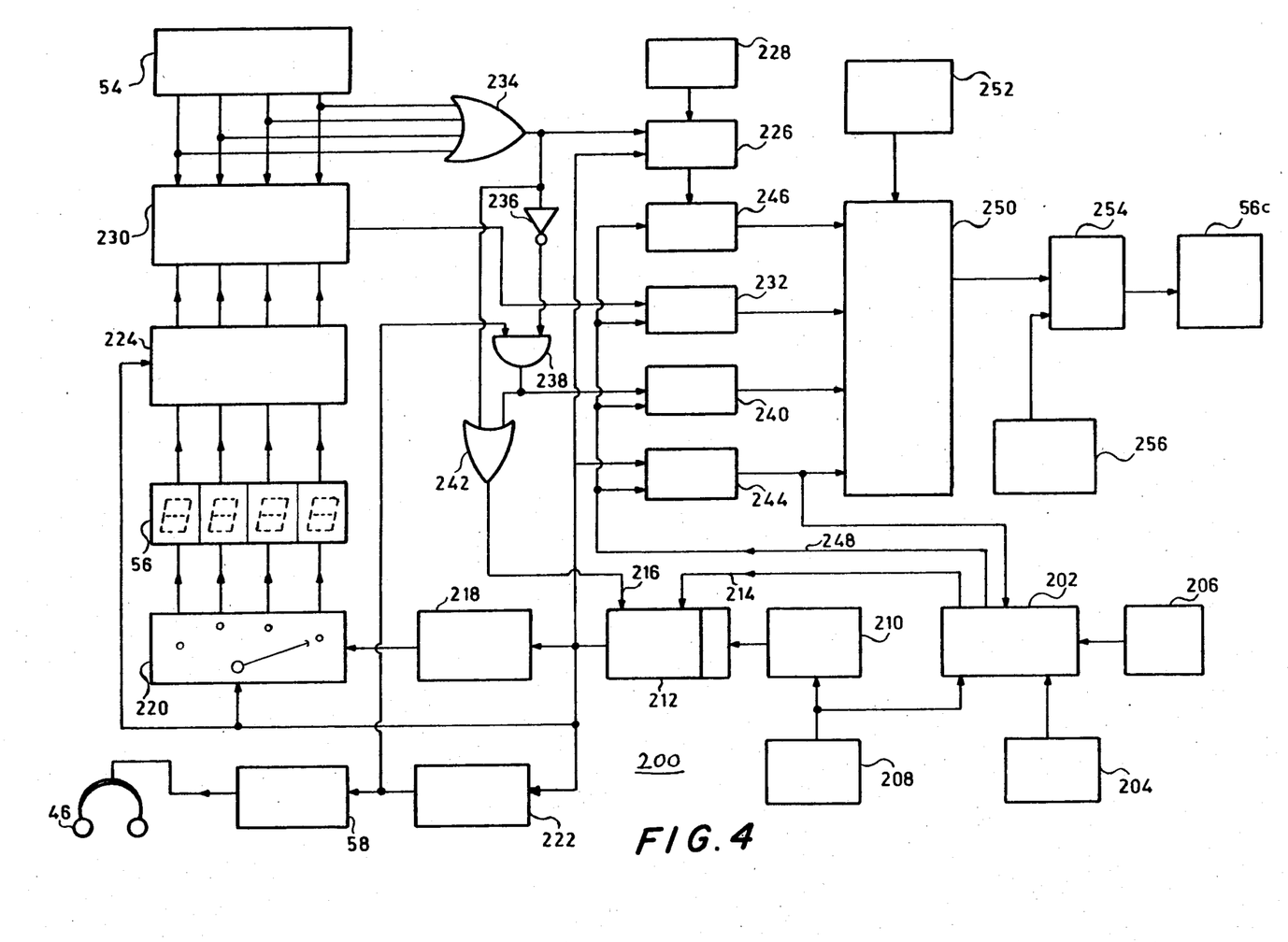
FIG. 4 shows the detailed block diagram of block 200 of FIG. 2.

The mental condition examination unit 200 shown in FIG. 4 comprises a control unit 202 connected to a pair of read only memories 204, 206 to store characteristic data for the subject (age, sex, occupation, atc.) and data defining the test rate being also dependent on the type of the examination. A start key 208 is coupled to the control unit 202 which can be made from a key of keyboard 54 (FIG. 2).

The start key 208 is connected to the control unit 202 and to starting input of a rate determining unit 210 which is designed as a generator providing linearly increasing voltages with an output coupled to timing input of a first random generator 212. The random generator 212 has a stop input controlled through line 214 by the control unit 202.

The first random generator 212 provides output pulses, which relative to a basic delay defined by the voltage applied to the timing input, have randomly changing actual delay times, and the reference moments from which the delays begin are defined by pulses coupled to trigger input 216 thereof. The first random generator 212 is designed to deliver an output pulse even if no trigger pulse is received within a predetermined time e.g. 2 s.

The output of the first random generator 212 delivers pulses with repetition times randomly fluctuating relative to a basic repetition time. This output is lead to six different branches.

First it is coupled to input of a second random generator 218 having random output signals defining the actual position of a four position switch 220. The random position control of the switch 220 occurs in such a way that an input signal coupled to the switch 220 can reach each of the four outputs with the same probability. It should be noted that the switch 220 and the second random generator 218 can be implemented by a common circuit. The four outputs of the switch 220 are coupled to respective inputs of the display segments 38 to 44 of the display 56 (FIG. 1), and the display segment activated in a random switch-position will flash for the duration of the output pulse of the first random generator 212 and displays a decimal number, e.g. a "0".

The output of the first random generator 212 is coupled to the input of the switch 220 in order that its pulse can get through to the display 56. This output is connected furthermore to input of a third random generator 222 which passes its input pulses in a random selection to its own output. The probability of the passage of the input pulses to the output is 50%. The output of the third random generator 222 is connected to the input of the acoustic coupler 58 (FIG. 2) which drives the headphone 46. This way an acoustical signal is generated if a pulse passes through the third random generator 222.

The output of the first random generator 212 is connected also to sampling input of a four-channel sample and hold circuit 224 to define the sampling moments thereof.

The fifth branching of the output of the first random generator 212 leads to starting input of a first counter 226. The input of the first counter 226 is coupled to output of a clock 228, and in enabled condition the counter 226 counts the clock pulses.

The sample and hold circuit 224 has four outputs coupled to four inputs of a first input group of a four-channel coincidence detector 230, which has a second input group with four inputs connected to respective key outputs of the keyboard 54 (FIG. 2). If an associated pair of inputs in the two groups of the coincidence detector 230 is activated simultaneously, then an output signal will be generated. This takes place if the flashing of a display segment is associated by the pushing of the corresponding key just under the segment. The output of the coincidence detector 230 is coupled to input of a second counter 232 to count the number of the right answers.

The respective outputs of the keyboard 54 are coupled to inputs of an OR gate 54, the output of which generates a pulse if any of the four keys has been pushed. This output is connected to stop input of the first counter 226 and through an OR gate 242 to the trigger input 216 of the first random generator 212. This latter connection provides for the fact that the next pulse of the first random generator 212 can be delivered only if a key has been pushed (within the waiting tolerance range of about 2 s).

The output of the OR gate 234 is coupled through inverter 236 to an input of AND gate 238. The other input of the AND gate 238 is connected to the output of the third random generator 222. The output of the AND gate is activated if an acoustical signal exists and no key is pushed. This, as it will be clear later, corresponds to an effective blocking because the subject under test has the standing instruction that if the optical display is associated with an acoustic signal, neither of the keys should be pushed. The output of the AND gate 238 is connected to the input of a third counter 240 which counts the number of effective blockings. In order to ensure that a next pulse be generated if an effective blocking takes place, the output of the AND gate 238 is coupled to an input of the OR gate 242 to pass a pulse to the trigger input 216 of the first random generator 212.

The sixth branching of the output of the first random generator 212 leads to input of a fourth counter 244 for counting all pulses (flashes).

The output of the first counter 226 is connected to input of an adder 246 to make and store the sum of the delay times. The enable inputs of the adder 246 and of the counters 232, 240 and 244 are coupled through line 248 to the output of the control unit 202.

The outputs of the adder 246 and of the counters 232, 240 and 244 are coupled to respective inputs of an arithmetical and logical unit 250 which has a further input connected with the output of a constant memory 252. The output of the arithmetical and logical unit 250 is connected to first input of a comparator 254 which has a second input connected to a second constant memory 256 and has an output coupled to display 56c which can be made by a segment of the display 56.

The operation of the mental condition examining unit 200 shown in FIG. 4 is as follows.

The subject under test has the task of watching the display 56, in which certain display segments will be illuminated in a random order and distribution by flashing out a decimal number (e.g. "0"). In response to each flash the subject has to push immediately the key associated with the activated display segment. If an acoustic signal is generated together with the visual display, then neither of the keys should be pushed. It is advisable if some experience is gathered in operating the apparatus before the mental condition test is made.

The test begins by pushing the start key 208. In response to the starting signal the rate determining unit 210 defines first longer, later gradually shortening intervals for the first random generator 212.

Reference is made now to FIG. 9 in which pulses L indicate the light signals and pulses K indicate key operations. First in moment $t_o$ a segment is flashed and the associated key is pushed in response thereto in moment $t_1$. The time elapsed between these two moments is defined as first reaction time Tr1. The random generator 212 generates the next light pulse in moment $t_2$, and a latent time TD1 is elapsed between the first response and the subsequent flash. During the measurement the latent time TD is gradually decreased, e.g. the i-th flash in moment $t_i$ is responded in moment $t_{i+1}$ and the next flash takes place in moment $t_{i+2}$ with latent time TDi which is shorter than the first latent time TD1.

This method provides a so called active time insufficiency for the subject because the rate depends on the speed of the response. If the subject fails to push any key, this fact will not stop the series of flashes, because in case of acoustic blockings the trigger input 216 of the random generator 212 will be activated by the output of the OR gate 242, and in other cases the next pulse is generated following the waiting period of maximum about 2 s.

The first counter 226 measures the reaction time Tr, since at the start of each illuminating pulse it gets a starting pulse and begins to count the pulses of the clock 228. When one of the keys has been pushed, the output of the OR gate 234 stops the counting operation. The next flash pulse starts the counter 226 again and it will measure the next reaction time. In each start the content of the counter 226 is read in the adder 246 which accumulates the pulse numbers corresponding to the series of reaction times Tr.

In case of a particular subject the starting latent time TD depends on many factors like age, sex, education, profession, etc. It can be preferable to begin the test with a comparatively longer latent time but to begin the actual measurements only in a later phase when the latent time TD is already shorter. The appropriate rate selection is facilitated by the data stored in the read only memories 204 and 206, and in response to these data the control unit enables the examination through the line 248 in the appropriate moments when the rate is suitable for the subject. The adder 246 and the counters 232, 240 and 244 start functioning only if an enable signal is delivered through the line 248. The measurement should be accomplished during a predetermined number of flashes which is typically 20. When the counter 244 reaches this number, it delivers a signal to the control unit 202 to stop the operation.

The second random generator 218 provides for the random distribution of the flashes among the four display segments. Following the starting of each flash pulse, the sample and hold circuit 224 receives a sample command to sample and store the actual condition of the output lines of the display 56 of which only one can be in on-condition. If in response to the flashing, the key is pushed which is associated with the active display segment, then the output of the coincidence detector 230 gets activated, whereby the counter 232 is increased and the right answer is recorded.

The acoustic blocking events are sensed by means of the counter 240. The counter 240 is stepped if there is no signal at the output of the OR gate 234 and there was an acoustic signal. This logical condition corresponds to an effective blocking, in which the reaction to the combined visual and acoustic signals was correct.

A value S2 characteristic to the actual mental condition can be defined by the following expression:

$$S2 = a_{21}\frac{T_{ri}}{N} + a_{22} RA + a_{23} EB \qquad (5)$$

In this expresssion (5) N designates the count in the counter 244 following the measurement i.e. the number of all visual flashings, $T_{ri}$ designates the sum of the respective reaction times which is given by the adder 246, RA designates the number of right answers obtained by the counter 232, and EB designates the number of effective blocks which is equal to the content of the counter 240.

The constant memory 252 supplies the values of the coefficients to the arithmetical and logical unit 250, and this latter receives all other data from the adder 246 and from the counters 232, 240 and 244, and it calculates and supplies the value S2.

It is true also for this examination that instead of accurate values, ranges like high, medium and low can give more adequate information on the actual condition. The actual range is determined by the comparator 254 depending on whether the value S2 is between two constant treshold values $K_{21}$ and $K_{22}$, or it is higher or lower than these values.

Typical values of the coefficients and constants for the mental condition examinations are as follows:

$$a_{21} = -64 \; a_{22} = +1 \; a_{23} = +1 \; K_{21} = +4.4 \; K_{22} = -1.6$$

These values can, of course, change depending on various factors like, sex, age, national character, profession etc.

The value S2 gives really a good indication on the mental condition, since the reaction time which is characteristic only to the motorial mechanism of the organization, has a negative weight in the expression, and if this motorial representation is deducted from the factor expressing the correctness of the selectional reaction test, a number is obtained which is characteristic to the mental information processing ability, and this ability is a feature which can not be derived directly by any kinds of tests or examinations. The mental information processing ability is a function of the actual mental condition. Similarly, the actual mental condition determines the extent how much the subject under test can process the acoustic blocking stimulations.

The above explanation (without referring to sophisticated interrelations in the field of information theory) tried to visualize for the reader that the value S2 is appropriate for expressing the actual mental condition, its determination is based on a scientific method, therefore this value has a general validity. Problematic can be the establishment of the coefficients and treshold values, however, the problem gets less complex with the usage of three qualifications only, although the measurement is capable of offering a finer evaluation.

Figure 5:
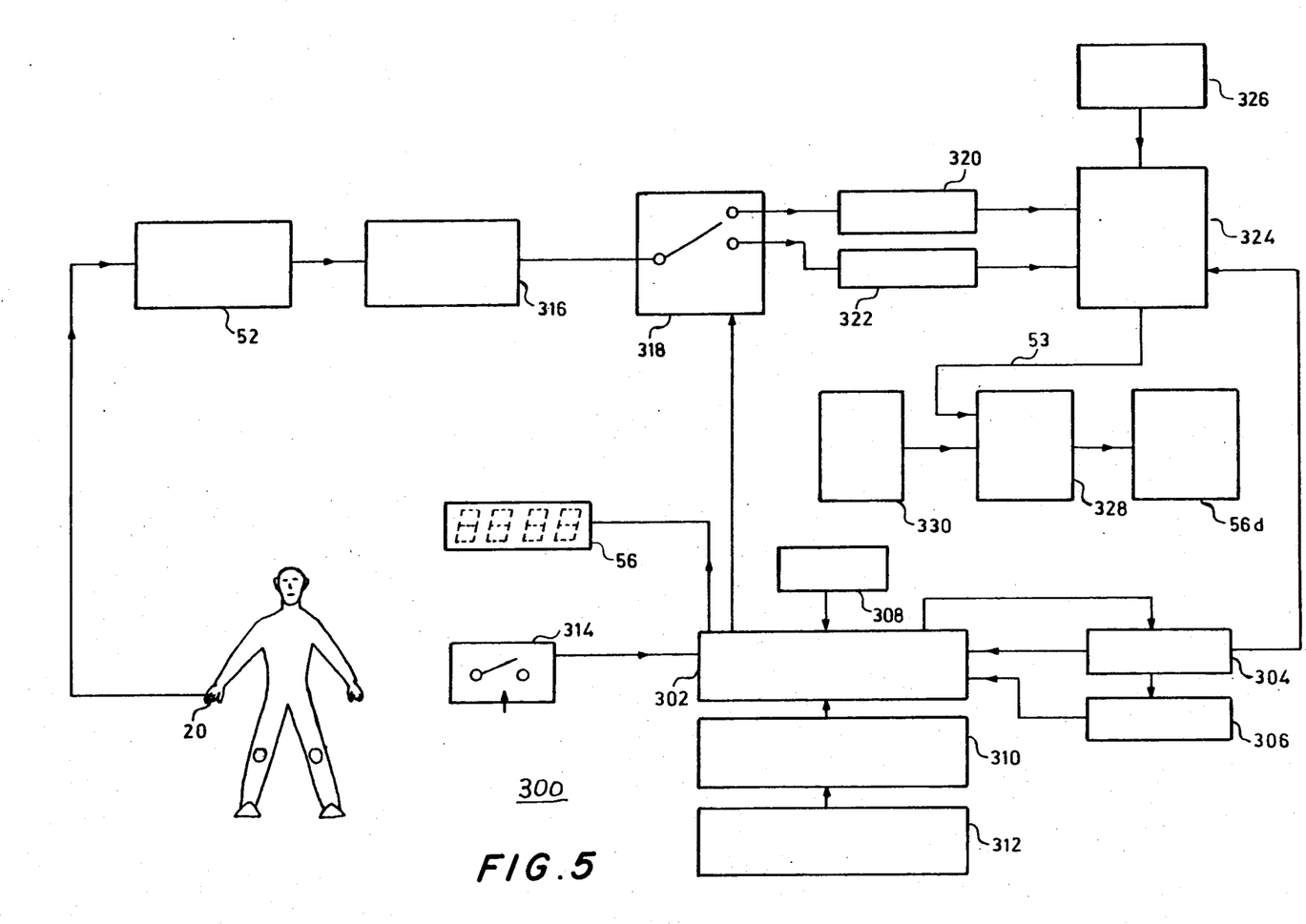
FIG. 5 shows the detailed block diagram of block 300 of FIG. 2.

Reference is made now to FIG. 5 which shows the block diagram of the physical condition examining unit 300 shown in FIG. 2.

The examination of the physical condition is based on measured values of the heart rate sampled following a physical load and a given rest thereafter. On the basis of characteristic data of the subject like weight, height, age, sex, etc. the number of physical excercises is determined by using an appropriate table. It is preferable if the excercises comprise crouch tasks which should be made as fast as possible. The crouch excercises should be made with the apparatus in hand, and the display shows preferably the number of excercises to be carried out and this value is decreased one by one following each succesful crouch. This decrease can be controlled manually by pushing a key at every excercise or automatically by means of an acceleration sensor.

The time required for completing a predetermined number of crouch excercises is measured, and the heart rate just after the excercises is also measured. This is followed by a rest phase for a predetermined time, whereafter the heart rate is measured again. The physical condition is determined on the basis of the two heart rate measurements and of the time elapsed between these measurements.

In FIG. 5 a control unit 302 is shown to which a first timer 304 and a second timer 306 triggered by the first one are connected. Start key 308 provides for triggering the starting moment. The data associated with the subject are stored in personal store 310 and in excercise store 312.

The pushing of the start key 308 results in the indication of the number N of the excercises to be carried out on the display 56 and in the start of the timing of the first timer 304. The subject starts making the crouch excercises and at each crouch an excercise sensor switch 314 delivers an indication to the control unit 302 which responds by decreasing the displayed value one by one.

When the predetermined number N of the excercises is completed, the first timer 304 receives a stop command and starts the second timer 306 which provides for a predetermined timing, e.g. for 2 minutes. The pulse sensor 20 and the heart rate measuring block 52 give directly or through a heart rate calculating unit 316 the actual heart rate value to switch 318 controlled by the control unit 302 in such a way that this heart rate value will be read in a first sample and store 320 receiving this time a sampling command.

When the second timer 306 provides the timing signal, the switch 318 changes over and connects a second sample and store 322 to the output of the heart rate calculating unit 316, and a sample command is delivered for reading the heart rate at the end of the relaxation phase in the second sample and store 322.

The time value stored in the first timer 304 and the values in the first and second sample and stores 320, 322 are passed to arithmetical and logical unit 324 which utilizes coefficients stored in constant memory 326 and generates a condition value S3.

The value S3 is passed to comparator 328 to be compared with treshold values stored in second constant memory 330, and the result of the comparison is applied to display 56d which can be made of a display segment of the display 56.

Figure 10:
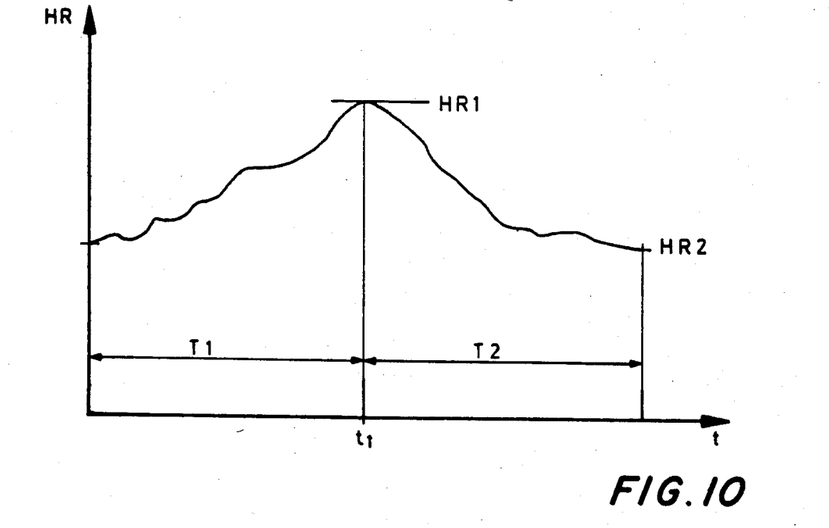
FIG. 10 shows the time curve of the heart rate value used for the physical condition test.

The curve of the heart rate during the examination is illustrated in FIG. 10. The heart rate increases during the excercises, and the predetermined number N of excercises is accomplished in moment $t_1$. The heart rate value HR1 in the end moment $t_1$ of the excercises and the duration T1 of the excercise phase are recorded. The excercise phase is followed by a relaxation (rest) phase for a time T2, and in the end moment of this phase the actual heart rate HR2 is measured and recorded.

In accordance with experimental tests the actual physical condition can well be represented by a value S3 defined as follows:

$$S3 = a_{31}HR1 + a_{32}T1 + a_{33}\frac{HR1 - HR2}{HR1} \qquad (6)$$

The value S3 is compared with two treshold values $K_{31}$ and $K_{32}$ to obtain discrete range values for the physical condition as it was described hereinabove in connection with the other two kinds of measurements.

Typical data for the constants in case of T2=2 minutes are as follows:

$a_{31} = -0.1$  $a_{32} = -0.1$  $a_{33} = +10$  $K_{31} = -8.2$
$K_{32} = -11.3$

Figure 7:
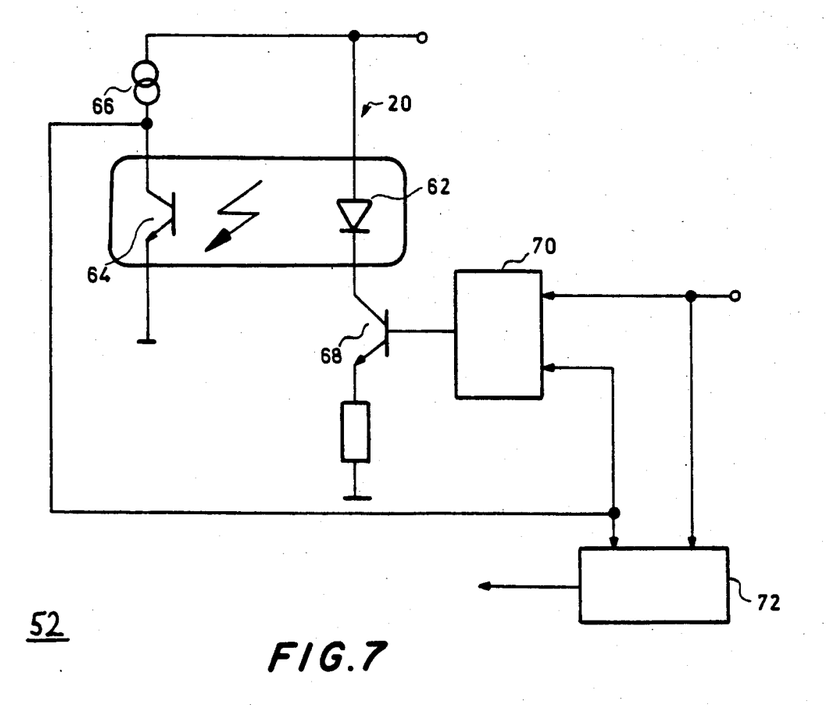
FIG. 7 shows a circuit arrangement usable for measuring the heart rate.

The apparatus shown in FIG. 5 can be implemented in several ways on the basis of the foregoing description, however, in view of the reliability of the measurements the actual design of the heart rate measuring block 52 is of outstanding significance. FIG. 7 shows a novel arrangement of the heart rate measuring block 52 which is believed to be suitable for performing reliable and accurate heart rate measurements.

The pulse sensor 20 has a conventional design and it comprises a light emitting diode 62 emitting light in the infrared range and a light sensitive transistor 64 arranged in the beam path. The diode 62 can be implemented e.g. by the device of TEXAS Instruments Inc. type TIL 31 and the transistor 64 can be made of the type TIL 81 of the same manufacturer.

A current generator 66 is arranged in the collector path of the transistor 64, and the collector voltage of the transistor 64 is determined by the amount of light flux which latter is dependent on the optical attenuation of the finger inserted in the beam path.

The current supply of the diode 62 is provided through a feedback loop and the light intensity thereof is dependent on the collector current of transistor 68. A regulating circuit with integrating output properties 70 is coupled to the base of the transistor 68 which has a time constant about 2 s. The regulating circuit 70 has a first input to which a voltage $V_o$ is applied and an other input connected to the collector of the transistor 64. The two inputs of the regulating circuit 70 are connected to inputs of a differential amplifier 72 having an output providing the heart rate signal.

The transistor 64 operates in optimum condition if the incident flux falls in the medium range of the light flux-collector current curve thereof. The current of the current generator 66 and the voltage $V_o$ are adjusted in such a way that in case of a finger with average transparency the light emitted by the diode 62 corresponds to the optimum working condition of the transistor 64. If the optical attenuation between the diode 62 and the transistor 64 is increased, the collector current of the transistor 64 decreases and the current generator 66 drives the current difference to the input resistor of the regulating circuit 70 (or to an other corresponding resistor not shown in the drawing). The voltage at the second input of the regulating circuit 70 will be increased compared to the voltage $V_o$, and the transistor 68 receives a higher driving current, whereby the current through the light emitting diode 62 and the light intensity thereof will increase and the transistor 64 is set closer to the optimum working point.

Owing to the time constant of about 2 s, the periodic changing of the transparency of the finger due to pulsation will not be followed by a corresponding fluctuation of the current of the transistor 68, which will always correspond to the average transparency of the finger. During pulsation the difference in the currents of the current generator 66 and of the transistor 64 generates a significant voltage difference between the two inputs of the differential amplifier 72, from which this latter can generate a definite heart rate signal.

By means of regulating the light of the diode 62 the circuit arrangement shown in FIG. 7 sets the transistor 64 always in the optimum working range. In spite of a changing or varying finger transparency the level of the pulse signal at the collector of the transistor 64 remains always in the well detectable range.

The technical solution according to the invention can be used in the first place in the combination as shown in FIGS. 1 and 2, in which it is capable of indicating the actual status of the biorythm of the subject. In the three main rythmical spheres, e.g. in the emotional, mental and physical ones the actual status of the subject is determined on the basis of objective measurements.

For the measurements of the individual conditions, the autonom blocks of the technical solution according to the invention can be used independently. It is also possible e.g. to give indication for the numerical values of the levels S1, S2 and S3 or to allocate these levels in a higher number of ranges. The autonom measurements are not influenced any more by the requirements connected with the small size, therefore e.g. the examination of the emotional condition can also be carried out on the basis of EEG spectrum analysis.

The details relating to the optimum measurements of the skin conductance and the heart rate in addition to their advantages in the applications described hereinabove, can well be used in other equipments or instruments, too.

We claim:

1. Apparatus for measuring the actual psychophysiological condition of a subject, comprising:
   a case to be held in hand;
   sensors engaging fingers holding the case to detect skin conductance;
   a pulse sensor engaging a finger holding the case;
   a keyboard arranged in a surface of the case with identical keys;
   a display arranged in said surface with display segments associated with respective ones of said keys;
   a block for determining the actual emotional condition which comprises:
      a skin conductance measuring block connected to said sensors,
      a feedback unit for delivering an indication for said subject in response to actual skin conductance values
   a block for determining the actual mental condition which comprises:
      a pulse source for providing light pulses on said display segments in a random distribution,
      an audio signal source providing audio signal together with selected ones of said light pulses according to a random selection,
      a means for detecting the simultaneous activation of a pair of associated key and display segment,
   a block for determining the actual physical condition which comprises:
      a heart rate measuring means associated with said pulse sensor,
      a means for determining the efficiency of repeated physical excercises made by said subject,
   an arithmetical and logical unit associated with said condition determining blocks for determing respective weighted sums of measuring results provided by said blocks.

2. The apparatus as claimed in claim 1, comprising memories associated with said condition determining blocks storing constant values depending on certain data of said subject, said constant values being supplied to said arithmetic and logical unit as weighting factors.

3. The apparatus as claimed in claim 2, comprising means for providing cathegories by comparing said weighted sums with predetermined treshold levels.

4. The apparatus as claimed in claim 1, comprising a single common arithmetical and logical unit, and a control unit for operating said blocks in accordance with tasks given for said subject.

* * * * *